(12) United States Patent
Zhang et al.

(10) Patent No.: US 10,947,175 B2
(45) Date of Patent: Mar. 16, 2021

(54) METHODS OF REMOVING CARBONYL-CONTAINING ORGANIC COMPOUNDS

(71) Applicant: Lyondell Chemical Technology, L.P., Houston, TX (US)

(72) Inventors: Lei Zhang, Houston, TX (US); Daniel F. White, Houston, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

(21) Appl. No.: 16/678,225

(22) Filed: Nov. 8, 2019

(65) Prior Publication Data

US 2020/0172460 A1    Jun. 4, 2020

Related U.S. Application Data

(60) Provisional application No. 62/773,791, filed on Nov. 30, 2018.

(51) Int. Cl.
*C07C 45/86* (2006.01)

(52) U.S. Cl.
CPC .................... *C07C 45/86* (2013.01)

(58) Field of Classification Search
CPC ..................................... C07C 45/86
See application file for complete search history.

(56) References Cited

U.S. PATENT DOCUMENTS

| | | |
|---|---|---|
| 4,075,256 A | 2/1978 | Foster et al. |
| 4,125,568 A | 11/1978 | Theriot et al. |
| 6,037,516 A | 3/2000 | Morford et al. |
| 2014/0141482 A1 | 5/2014 | Pearlman et al. |
| 2015/0112107 A1 | 4/2015 | Ramesh et al. |
| 2017/0050902 A1 | 2/2017 | Kurukchi et al. |
| 2017/0137349 A1 | 5/2017 | Kurukchi et al. |

FOREIGN PATENT DOCUMENTS

| | | |
|---|---|---|
| WO | 9926937 A1 | 6/1999 |
| WO | 2013098273 A1 | 7/2013 |

OTHER PUBLICATIONS

The International Search Report and The Written Opinion for PCT/US2019/060601 dated Feb. 26, 2020.

*Primary Examiner* — Sikarl A Witherspoon

(57) ABSTRACT

Provided are methods of treating a mixture, such as a hydrocarbon mixture, that includes one or more C2-C4 carbonyl containing organic compounds. The methods may include contacting a hydrocarbon mixture with an aqueous liquid including an agent. The agent may reduce the amount of one or more C2-C4 carbonyl containing organic compounds in the mixture.

20 Claims, 1 Drawing Sheet

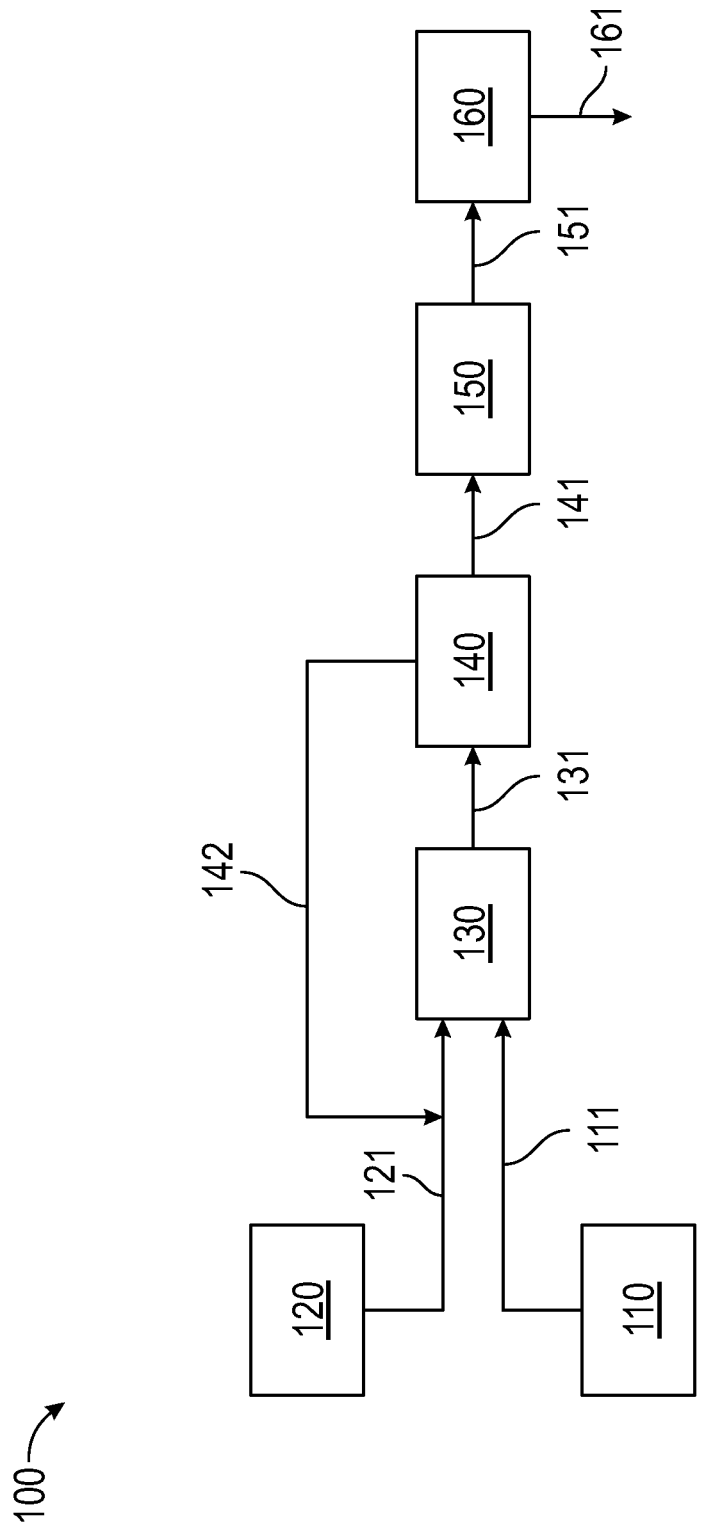

METHODS OF REMOVING CARBONYL-CONTAINING ORGANIC COMPOUNDS

CROSS-REFERENCE TO RELATED APPLICATIONS

This application is the Non-Provisional Patent Application, which claims benefit of priority to U.S. Provisional Application No. 62/773,791, filed Nov. 30, 2018, the contents of which are incorporated herein by reference in their entirety.

BACKGROUND

Butadiene is an important commodity chemical, especially in the tire industry. Butadiene is typically a byproduct that is present in crude mixtures produced from ethylene production and/or processing.

The hydrocarbon mixture commonly referred to as "crude C4" typically includes various paraffins (e.g., n-C4 and i-C4), olefins (e.g., 1-butene (B1), 2-butene (B2), and isobutene), butadiene, and usually small amounts of acetylenes (e.g., MAPD (methyl acetylene and propadiene)). When recovered from ethylene production, crude C4 also may include carbonyl-containing organic compounds. The presence of carbonyl-containing organic compounds can be undesirable, because the carbonyl-containing organic compounds may promote polymerization in extractive distillation and butadiene product columns.

Certain processes that produce crude C4, including renewable processes, can result in the presence of a variety of carbonyl-containing organic compounds, including carbonyl-containing organic compounds having 2 to 4 carbon atoms. The carbonyl-containing organic compounds that may be present in crude C4 produced from renewable processes may differ, at least partially, from the carbonyl-containing organic compounds that may be present in crude C4 recovered from other processes, including non-renewable processes.

The carbonyl-containing organic compounds that may be present in crude C4 produced by renewable processes can include, but are not limited to, acetaldehyde, acrolein, 3-buten-2-one, crotonaldehyde, or a combination thereof. These carbonyl-containing organic compounds generally exist in larger quantities in the crude C4 collected from renewable processes compared to other processes, and/or may generally have a "bulkier" structure (e.g., greater molecular weight and/or more steric hindrance, etc.) than the carbonyl-containing organic compounds collected from other processes.

Therefore, there remains a need for methods of reducing or eliminating the presence of carbonyl-containing organic compounds from products, such as crude C4, including crude C4 produced by renewable processes.

BRIEF SUMMARY

Provided herein are methods of treating mixtures, embodiments of which can substantially eliminate or reduce an amount of one or more C2-C4 carbonyl-containing organic compounds in the mixtures. Embodiments of the methods provided herein are surprisingly effective at substantially removing or reducing an amount of the "bulkier" (e.g., greater molecular weight and/or more steric hindrance, etc.) C2-C4 carbonyl-containing organic compounds that typically are present in crude C4 obtained from renewable processes.

In one aspect, methods of treating mixtures are provided. In embodiments, the methods include providing a hydrocarbon mixture including one or more C2-C4 carbonyl-containing organic compounds; and contacting the hydrocarbon mixture with an aqueous liquid including an agent, the agent including sodium sulfite ($Na_2SO_3$), sodium bisulfite ($NaHSO_3$), sodium metabisulfite ($Na_2S_2O_5$), sodium borohydride ($NaBH_4$), dimethylacetamide ($CH_3CN(CH_3)_2$), or a combination thereof; wherein the one or more C2-C4 carbonyl-containing organic compounds include propanal, propenal, butanone, butenone, butanal, butenal, or a combination thereof. The methods also may include separating the hydrocarbon mixture and the aqueous liquid to form a product hydrocarbon mixture.

In some embodiments, the methods include providing a hydrocarbon mixture, the hydrocarbon mixture including [1] about 5 wtppm to about 200 wtppm of acrolein, [2] about 5 wtppm to about 200 wtppm of 3-buten-2-one, [3] about 5 wtppm to about 200 wtppm of crotonaldehyde, or [4] a combination thereof; contacting the hydrocarbon mixture with an aqueous liquid including an agent, the agent including sodium sulfite ($Na_2SO_3$), sodium bisulfite ($NaHSO_3$), sodium metabisulfite ($Na_2S_2O_5$), sodium borohydride ($NaBH_4$), dimethylacetamide ($CH_3CN(CH_3)_2$), or a combination thereof; and separating the hydrocarbon mixture and the aqueous liquid to form a product hydrocarbon mixture; wherein the product hydrocarbon mixture includes at least one of acrolein, 3-buten-2-one, or crotonaldehyde at a concentration of 0 wtppm to about 3 wtppm.

In additional embodiments, the methods include providing a hydrocarbon mixture, the hydrocarbon mixture including one or more C2-C4 carbonyl-containing organic compounds, wherein at least one of the one or more C2-C4 carbonyl-containing organic compounds is present at a concentration of about 5 wtppm to about 200 wtppm; contacting the hydrocarbon mixture with an aqueous liquid including an agent, the agent including sodium sulfite ($Na_2SO_3$), sodium bisulfite ($NaHSO_3$), sodium metasulfite ($Na_2S_2O_5$), sodium borohydride ($NaBH_4$), dimethylacetamide ($CH_3CN(CH_3)_2$), or a combination thereof; separating the hydrocarbon mixture and the aqueous liquid to form a product hydrocarbon mixture; wherein the product hydrocarbon mixture includes 0 wtppm to about 3 wtppm of the C2-C4 carbonyl-containing organic compound that was present in the hydrocarbon mixture at a concentration of about 5 wtppm to about 200 wtppm.

Other objects, features, and advantages of the invention will be apparent from the following detailed description, drawings, and claims. Unless otherwise defined, all technical and scientific terms and abbreviations used herein have the same meaning as commonly understood by one of ordinary skill in the art to which this invention pertains. Although methods and compositions similar or equivalent to those described herein can be used in the practice of the present invention, suitable methods and compositions are described without intending that any such methods and compositions limit the invention herein.

BRIEF DESCRIPTION OF THE DRAWINGS

The FIGURE depicts an embodiment of a system for processing crude C4.

DETAILED DESCRIPTION

Provided herein are methods of treating mixtures, and embodiments of the methods are capable of substantially eliminating or reducing an amount of one or more carbonyl-containing organic compounds in the mixtures.

A carbonyl-containing organic compound is "substantially eliminate[ed]" from a mixture when its concentration in the mixture, after treatment, is 0 wtppm to about 1 wtppm, or, in some instances, beyond the detection limit of a particular instrument. In some embodiments, the amount or concentration of one or more carbonyl-containing organic compounds is reduced by about 80% to 100%, about 90% to 100%, about 95% to 100%, about 98% to 100%, or about 99% to 100%. For example, if a carbonyl-containing organic compound is initially present at a concentration of 50 wtppm and its concentration after treatment is 1 wtppm, then the concentration of the carbonyl-containing organic compound has been reduced by 98%.

In embodiments, the methods provided herein include providing a hydrocarbon mixture including one or more C2-C4 carbonyl-containing organic compounds; and contacting the hydrocarbon mixture with an aqueous liquid including an agent, the agent including sodium sulfite ($Na_2SO_3$), sodium bisulfate ($NaHSO_3$), sodium metabisulfite ($Na_2S_2O_5$), sodium borohydride ($NaBH_4$), dimethylacetamide ($CH_3CN(CH_3)_2$), or a combination thereof; wherein the one or more C2-C4 carbonyl-containing organic compounds include propanal, propenal, butanone, butenone, butanal, butenal, or a combination thereof.

Generally, the contacting of the hydrocarbon mixture with the aqueous liquid may occur at any conditions sufficient to maintain the hydrocarbon mixture in a liquid state. In some embodiments, the contacting of the hydrocarbon mixture with the aqueous liquid occurs at ambient temperature and ambient pressure. In further embodiments, the contacting of the hydrocarbon mixture with the aqueous liquid occurs at ambient temperature and a pressure greater than the pressure at ambient temperature. The pressure greater than the pressure at ambient temperature, for example, may be about 15 psig to about 100 psig, about 15 psig to about 90 psig, about 15 psig to about 80 psig, about 15 psig to about 70 psig, about 15 psig to about 60 psig, about 15 psig to about 50 psig, about 15 psig to about 40 psig, about 15 psig to about 30 psig, or about 15 psig to about 20 psig.

As used herein, ambient temperature and ambient pressure may refer to standard ambient temperature and pressure. Standard ambient temperature and pressure is a temperature of 25° C. (298.15 K, 68° F.) and a pressure of 1 atm (101.325 kPa, 101.325 $kN/m^2$, 0 psig).

The contacting of the hydrocarbon mixture with the aqueous liquid may include mixing the hydrocarbon mixture and the aqueous liquid. The mixing of the hydrocarbon mixture and the aqueous liquid may be achieved by any known techniques and/or using any known equipment. For example, the hydrocarbon mixture and the aqueous liquid may be mechanically stirred. As a further example, a static mixture may be used to mix the hydrocarbon mixture and the aqueous liquid.

The hydrocarbon mixture generally may be contacted with any amount of aqueous liquid. The amount of aqueous liquid may be selected based on one or more factors, including, but not limited to, the concentration of agent in an aqueous liquid, the concentration of C2-C4 carbonyl-containing organic compounds in a hydrocarbon mixture, desired reaction time, reaction conditions, etc. In some embodiments, the hydrocarbon mixture and the aqueous liquid are present at a volume ratio of about 0.5:1 to about 1.5:1. In additional embodiments, the hydrocarbon mixture and the aqueous liquid are present at a volume ratio of about 0.8:1 to about 1.5:1. In further embodiments, the hydrocarbon mixture and the aqueous liquid are present at a volume ratio of about 0.5:1 to about 1.2:1. In still further embodiments, the hydrocarbon mixture and the aqueous liquid are present at a volume ratio of about 0.8:1 to about 1.2:1. In particular embodiments, the hydrocarbon mixture and the aqueous liquid are present at a volume ratio of about 0.8:1 to about 1:1. In several embodiments, the hydrocarbon mixture and the aqueous liquid are present at a volume ratio of about 1:1 to about 1.2:1. In one embodiment, the hydrocarbon mixture and the aqueous liquid are present at a volume ratio of about 1:1.

Nucleophilic Agents

The agents of the methods provided herein may include nucleophilic agents, such as sodium sulfite ($Na_2SO_3$), sodium bisulfite ($NaHSO_3$), sodium metabisulfite ($Na_2S_2O_5$), sodium borohydride ($NaBH_4$), dimethylacetamide ($CH_3CN(CH_3)_2$), or a combination thereof. In one embodiment, the agent is sodium sulfite ($Na_2SO_3$). In one embodiment, the agent is sodium bisulfite ($NaHSO_3$). In another embodiment, the agent is sodium metabisulfite ($Na_2S_2O_5$). In a further embodiment, the agent is sodium borohydride ($NaBH_4$). In yet another embodiment, the agent is dimethylacetamide ($CH_3CN(CH_3)_2$).

The aqueous liquids of the methods provided herein generally include water and an agent. The agent generally may be present in an aqueous liquid at any concentration that will permit the agent to dissolve in the aqueous liquid. In some embodiments, the agent is present in the aqueous liquid at an amount of about 10% to about 30% by weight, based on the total weight of the aqueous liquid and the agent. In further embodiments, the agent is present in the aqueous liquid at an amount of about 15% to about 25% by weight, based on the total weight of the aqueous liquid and the agent. In still further embodiments, the agent is present in the aqueous liquid at an amount of about 15% to about 20% by weight, based on the total weight of the aqueous liquid and the agent. One or more additives also may be present in the aqueous liquids provided herein.

Carbonyl-Containing Organic Compounds

Generally, the C2-C4 carbonyl-containing organic compounds may include any compounds having at least one carbonyl functional group and two to four carbon atoms. One of the two to four carbon atoms is the carbon atom of the at least one carbonyl functional group. Non-limiting examples of C2-C4 carbonyl-containing organic compounds include those disclosed, for example, in U.S. Patent Application Publication No. 2014/0141482, which is incorporated by reference.

The C2-C4 carbonyl-containing organic compounds that may be included in the hydrocarbon mixtures herein include, but are not limited to, the following and isomers thereof:

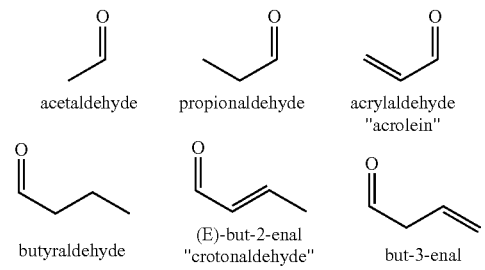

acetaldehyde  propionaldehyde  acrylaldehyde "acrolein"

butyraldehyde  (E)-but-2-enal "crotonaldehyde"  but-3-enal

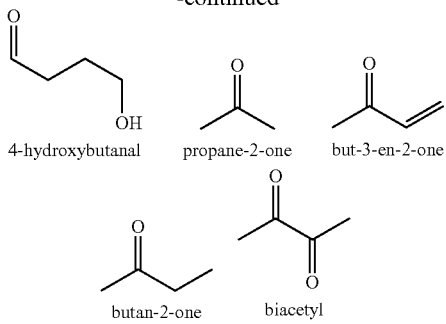

In some embodiments, the one or more C2-C4 carbonyl-containing organic compounds of the hydrocarbon mixtures include acetaldehyde, propenal (i.e., acrolein), 3-buten-2-one, crotonaldehyde, or a combination thereof. In one embodiment, the one or more C2-C4 carbonyl-containing organic compounds include acetaldehyde, propenal, 3-buten-2-one, and crotonaldehyde.

Not wishing to be bound by any particular theory, embodiments of the methods herein may function, at least in part, due to a reaction between a sulfite nucleophile and a carbonyl functional group. For example, the nucleophilic addition of a sulfite to acetone is depicted at Scheme 1.

Scheme 1 Possible mechanism of a nucleophilic addition of sulfite to acetone.

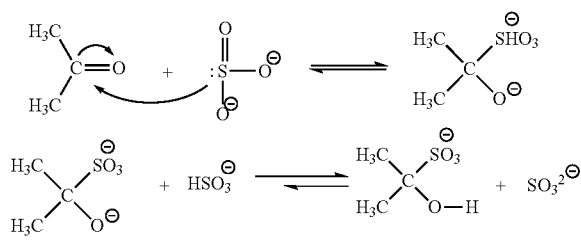

The mechanism depicted at Scheme 1 also may apply to a nucleophilic addition of sulfite to an aldehyde. Aldehydes, at least in some embodiments, may be more susceptible to the nucleophilic addition of sulfites than ketones, due, at least in part, to differences in steric hindrance. Nevertheless, embodiments of the methods provided herein are surprisingly effective for both aldehydes and ketones. In some embodiments, the methods provided herein also are surprisingly effective at substantially removing or reducing an amount of the "bulkier" (e.g., greater molecular weight and/or more steric hindrance, etc.) C2-C4 carbonyl-containing organic compounds that typically are present in crude C4 obtained from renewable processes.

Hydrocarbon Mixtures

The hydrocarbon mixtures including one or more C2-C4 carbonyl-containing organic compounds may include hydrocarbon mixtures that are products or byproducts of a chemical process. In some embodiments, the hydrocarbon mixtures are "crude C4" mixtures. The "crude C4" mixtures may be the byproduct of ethylene production or processing, including renewable processes. The hydrocarbon mixtures may include one or more of the following materials: C4 paraffins, C4 olefins, butadiene, and acetylenes.

Generally, each of the one or more C2-C4 carbonyl-containing organic compounds may be independently present in the hydrocarbon mixtures at any amount. In embodiments, each of the one or more C2-C4 carbonyl-containing organic compounds is independently present in a hydrocarbon mixture at an amount of about 5 wtppm to about 200 wtppm, about 5 wtppm to about 150 wtppm, about 5 wtppm to about 100 wtppm, about 5 wtppm to about 75 wtppm, about 5 wtppm to about 50 wtppm, or about 5 wtppm to about 25 wtppm. For example, if three C2-C4 carbonyl-containing organic compounds are "independently present" in a hydrocarbon mixture at an amount of "about 5 wtppm to about 25 wtppm", then the three C2-C4 carbonyl-containing organic compounds may be present at different concentrations in the hydrocarbon mixture, such as 10 wtppm, 15 wtppm, and 20 wtppm, respectively.

In some embodiments, the one or more C2-C4 carbonyl-containing organic compounds of the hydrocarbon mixtures include acetaldehyde, propenal, 3-buten-2-one, crotonaldehyde, or a combination thereof; and the acetaldehyde, the propenal, the 3-buten-2-one, and the crotonaldehyde are independently present in the hydrocarbon mixtures at amounts of about 5 wtppm to about 200 wtppm, about 5 wtppm to about 150 wtppm, about 5 wtppm to about 100 wtppm, about 5 wtppm to about 75 wtppm, about 5 wtppm to about 50 wtppm, or about 5 wtppm to about 25 wtppm. In one embodiment, the one or more C2-C4 carbonyl-containing organic compounds of the hydrocarbon mixtures include acetaldehyde, propenal, 3-buten-2-one, crotonaldehyde, or a combination thereof; and the acetaldehyde, the propenal, the 3-buten-2-one, and the crotonaldehyde are independently present in the hydrocarbon mixtures at amounts of about 5 wtppm to about 25 wtppm.

Product Hydrocarbon Mixtures

The methods also may include separating the hydrocarbon mixture and the aqueous liquid to form a product hydrocarbon mixture. The separating of the hydrocarbon mixture and the aqueous liquid may be achieved using any known techniques or equipment. For example, a settling drum may be used to separate the hydrocarbon mixture and the aqueous liquid. A settling drum used to separate the hydrocarbon mixture and the aqueous liquid may be under pressure.

An amount of at least one C2-C4 carbonyl-containing organic compound in the product hydrocarbon mixture may be less than the amount in the hydrocarbon mixture prior to treatment, i.e., the contacting of the hydrocarbon mixture with the aqueous liquid that includes an agent.

In some embodiments, an amount of the one or more C2-C4 carbonyl-containing organic compounds that is present in the product hydrocarbon mixture is about 80% to 100% less than an amount of the one or more C2-C4 carbonyl-containing organic compounds in the hydrocarbon mixture.

In some embodiments, an amount of the one or more C2-C4 carbonyl-containing organic compounds that is present in the product hydrocarbon mixture is about 95% to 100% less than an amount of the one or more C2-C4 carbonyl-containing organic compounds in the hydrocarbon mixture.

In some embodiments, an amount of the one or more C2-C4 carbonyl-containing organic compounds that is present in the product hydrocarbon mixture is about 98% to 100% less than an amount of the one or more C2-C4 carbonyl-containing organic compounds in the hydrocarbon mixture.

In some embodiments, after the contacting of the hydrocarbon mixture with the aqueous liquid, at least one of the one or more C2-C4 carbonyl-containing organic compounds is present in the hydrocarbon mixture at an amount of 0 wtppm to about 5 wtppm, 0 wtppm to about 4 wtppm, 0 wtppm to about 3 wtppm, 0 wtppm to about 2 wtppm, 0 wtppm to about 1 wtppm, or 0 wtppm to about 0.1 wtppm.

In some embodiments, the methods provided herein include providing a hydrocarbon mixture, the hydrocarbon mixture including [1] about 5 wtppm to about 200 wtppm of acrolein, [2] about 5 wtppm to about 200 wtppm of 3-buten-2-one, [3] about 5 wtppm to about 200 wtppm of crotonaldehyde, or [4] a combination thereof; contacting the hydrocarbon mixture with an aqueous liquid including an agent, the agent including sodium sulfite ($Na_2SO_3$), sodium bisulfate ($NaHSO_3$), sodium metabisulfite ($Na_2S_2O_5$), sodium borohydride ($NaBH_4$), dimethylacetamide ($CH_3CN(CH_3)_2$), or a combination thereof; and separating the hydrocarbon mixture and the aqueous liquid to form a product hydrocarbon mixture; wherein the product hydrocarbon mixture includes at least one of acrolein, 3-buten-2-one, or crotonaldehyde at a concentration of 0 wtppm to about 3 wtppm. In one embodiment, the product hydrocarbon mixture includes [1] 0 wtppm to about 3 wtppm of acrolein, [2] 0 wtppm to about 3 wtppm of 3-buten-2-one, and [3] 0 wtppm to about 3 wtppm of crotonaldehyde. In another embodiment, the product hydrocarbon mixture includes at least one of acrolein, 3-buten-2-one, or crotonaldehyde at a concentration of 0 wtppm to about 1 wtppm. In yet another embodiment, the product hydrocarbon mixture includes [1] less than about 3 wtppm of acrolein, [2] less than about 3 wtppm of 3-buten-2-one, and [3] less than about 3 wtppm of crotonaldehyde.

In some embodiments, the methods provided herein include providing a hydrocarbon mixture, the hydrocarbon mixture including one or more C2-C4 carbonyl-containing organic compounds, wherein at least one of the one or more C2-C4 carbonyl-containing organic compounds is present at a concentration of about 5 wtppm to about 200 wtppm; contacting the hydrocarbon mixture with an aqueous liquid including an agent, the agent including sodium sulfite ($Na_2SO_3$), sodium bisulfite ($NaHSO_3$), sodium metasulfite ($Na_2S_2O_5$), sodium borohydride ($NaBH_4$), dimethylacetamide ($CH_3CN(CH_3)_2$), or a combination thereof; separating the hydrocarbon mixture and the aqueous liquid to form a product hydrocarbon mixture; wherein the product hydrocarbon mixture includes 0 wtppm to about 3 wtppm of the C2-C4 carbonyl-containing organic compound that was present in the hydrocarbon mixture at a concentration of about 5 wtppm to about 200 wtppm. In one embodiment, the product hydrocarbon mixture includes 0 wtppm to about 1 wtppm of the C2-C4 carbonyl-containing organic compound that was present in the hydrocarbon mixture at a concentration of about 5 wtppm to about 200 wtppm.

The methods herein may be incorporated into methods and systems for processing crude C4. For example, a crude C4 feed may be subjected to one or more of the methods provided herein before the crude C4 feed is subjected to further processing, including, but not limited to, one or more of acetylene hydrogenation, butadiene extraction, etc.

An embodiment of a system for processing crude C4 is depicted at the FIGURE. The system 100 of the FIGURE includes a crude C4 source 110 and a source 120 of an aqueous liquid including an agent. The crude C4 source 110 provides a crude C4 feed 111 to an inline static mixer 130, and the source 120 of the aqueous liquid including an agent provides a feed 121 of the aqueous liquid including an agent to the inline static mixer 130.

The crude C4 feed 111 may be provided to the inline static mixer 130 at a rate of about 600 GPM (gallons per minute) to about 1000 GPM. In one embodiment, the crude C4 feed 111 is provided to the inline static mixer 130 at a rate of about 800 GPM.

The feed 121 of the aqueous liquid including an agent may be provided to the inline static mixer 130 at a rate of about 2 GPM to about 6 GPM. In one embodiment, the feed 121 of the aqueous liquid including an agent is provided to the inline static mixer 130 at a rate of about 4 GPM.

The inline static mixer 130 produces a mixed feed 131 that is provided to a settling drum 140 that separates the aqueous and organic phases of the mixed feed 131. The organic phase 141 is fed to an acetylene hydrogenation apparatus 150. At least a portion of the aqueous phase of the mixed feed 131 is provided as a recycled feed 142 to feed 121 of an aqueous liquid including an agent. The recycled feed 142 may be the product of a 20 GPM recycle.

The settling drum 140 may operate an ambient temperature and pressure, or at ambient temperature and an increased pressure, such as about 15 psig to about 100 psig. In one embodiment, the settling drum 140 operates an ambient temperature and a pressure of about 70 psig.

The acetylene hydrogenation apparatus 150 produces a feed 151 that is fed to a butadiene extraction apparatus 160 that produces a butadiene product 161.

It must be noted that, as used in the written description and the appended claims, the singular forms "a," "an," and "the" include plural referents unless the context clearly dictates otherwise. Thus, for example, reference to "an aromatic compound" includes mixtures of aromatic compounds, and the like.

The term "about" means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. Whether or not modified by the term "about", the claims include equivalents to the quantities. The term "about" may mean within 10% of the reported numerical value, or within 5% of the reported numerical value, or within 2% of the reported numerical value.

For any particular compound disclosed herein, any general structure presented also encompasses all conformational isomers, regioisomers, and stereoisomers that may arise from a particular set of substituents. Thus, the general structure also encompasses all enantiomers, diastereomers, and other optical isomers whether in enantiomeric or racemic forms, as well as mixtures of stereoisomers, as the context requires.

Various numerical ranges may be disclosed herein. When Applicant discloses or claims a range of any type, Applicant's intent is to disclose or claim individually each possible number that such a range could reasonably encompass, including end points of the range as well as any sub-ranges and combinations of sub-ranges encompassed therein, unless otherwise specified. Moreover, all numerical end points of ranges disclosed herein are approximate. As a representative example, Applicant discloses, in one embodiment, that "each of the one or more C2-C4 carbonyl-containing organic compounds is independently present in the hydrocarbon mixture at an amount of about 5 wtppm to about 25 wtppm". This range should be interpreted as encompassing values in a range of about 5 wtppm and about 25 wtppm, and further encompasses "about" each of 6 wtppm, 7 wtppm, 8 wtppm, 9 wtppm, 10 wtppm, 11 wtppm, 12 wtppm, 13 wtppm, 14 wtppm, 15 wtppm, 16 wtppm, 17 wtppm, 18 wtppm, 19 wtppm, 20 wtppm, 21 wtppm, 22 wtppm, 23 wtppm, and 24 wtppm, including any ranges and sub-ranges between any of these values.

The processes described herein may be carried out or performed in any suitable order as desired in various implementations. Additionally, in certain implementations, at least a portion of the processes may be carried out in parallel. Furthermore, in certain implementations, less than or more than the processes described may be performed.

Many modifications and other implementations of the disclosure set forth herein will be apparent having the benefit of the teachings presented in the foregoing descriptions and the associated drawings. Therefore, it is to be understood that the disclosure is not to be limited to the specific implementations disclosed and that modifications and other implementations are intended to be included within the scope of the appended claims

EXAMPLES

The present invention is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims. Thus, other aspects of this invention will be apparent to those skilled in the art from consideration of the specification and practice of the invention disclosed herein.

Example 1—Removal of Organic Carbonyls from 1-Octene

In this example, the removal of specific organic carbonyls in 1-octene was investigated. The results of the example showed a substantially complete removal of the tested compounds, which, for this example, included [1] acetaldehyde, [2] acrolein, [3] 3-butene-2-one, and [4] crotonaldehyde. 1-Octene was used in this example to simulate a crude C4 matrix contaminated with carbonyl-containing organic compounds.

These compounds were initially present in the 1-octene at an amount of about 10 wtppm each, and treatment of the 1-octene with an aqueous sodium bisulfite solution removed substantially all of the tested compounds.

The experiments of this example were conducted under ambient conditions.

For this example, $NaHSO_3$ (ACS reagent), acetaldehyde (CAS 75-07-0), acrolein (CAS 107-02-8), 3-buten-2-one (CAS 78-94-4), and crotonaldehyde (CAS 123-73-9) were purchased from Sigma-Aldrich, and used as received. Acetone (CAS 67-64-1) and 1-octene were purchased from Fisher, and used as received.

Deionized (DI) water was used to prepare the sodium bisulfite solutions of this example. A 17 wt % $NaHSO_3$ aqueous solution was prepared. 93.26 g of $NaHSO_3$ solid was weighed into a 1 L bottle followed by 416.61 g DI water to produce a clear colorless solution.

For this example, three 1-octene samples were prepared. The first 1-octene sample included 100 wtppm of acetaldehyde and 100 wtppm of acetone. The second 1-octene sample included 50 wtppm of acetaldehyde, 50 wtppm of acrolein, 50 wtppm of 3-buten-2-one, and 50 wtppm of crotonaldehyde. The third 1-octene sample included 10 wtppm of acetaldehyde, 10 wtppm of acrolein, 10 wtppm of 3-buten-2-one, and 10 wtppm of crotonaldehyde. The samples were submitted for gas chromatography (GC) analysis to determine quantitatively the amounts of carbon-containing organic compounds in each sample. The GC-determined quantities appear in Tables 1 and 2.

The three 1-octene samples were subjected to the following general procedure. 50 mL of the sodium bisulfite solution and a magnetic stirrer were added to a 250 mL Erlenmeyer flask, followed by 50 mL of one of the three 1-octene samples. The resulting mixture was stirred at ambient temperature and pressure for 3 to 5 minutes. The organic and aqueous phases then were separated with a separation funnel. The 1-octene samples were subjected to GC analysis before and after being mixed with the aqueous sodium bisulfite solution.

The results achieved by the 17 wt % sodium bisulfite solution were compared with those achieved by a similar sodium bisulfite solution containing 15 wt % $Na_2SO_3$ and 5 wt % $NaHSO_3$. The 1-octene sample containing 100 wtppm of acetaldehyde and 100 wtppm of acetone were mixed with these two sodium bisulfite solutions according to the general procedure of this example.

The results from these tests are depicted at Table 1.

TABLE 1

Presence of carbonyl-containing organic compounds before and after sodium bisulfite washes, as determined by GC

| Na Bisulfite Solution | Before/After Wash | Acetaldehyde (wtppm) | Acetone (wtppm) |
|---|---|---|---|
| 17 wt % $NaHSO_3$ | Before | 101 | 85 |
| | After | 0 | 0 |
| 15 wt % $Na_2SO_3$ 5 wt % $NaHSO_3$ | Before | 113 | 87 |
| | After | 0 | 0 |

The results of Table 1 demonstrate that both aqueous solutions led to a substantially complete removal of acetaldehyde and acetone from the 1-octene.

The 17 wt % $NaHSO_3$ solution also was used to wash 1-octene solutions containing acetaldehyde, acrolein, 3-buten-2-one, and crotonaldehyde. The results of these tests are provided at Table 2.

TABLE 2

Presence of acetaldehyde, acrolein, 3-buten-2-one, and crotonaldehyde before and after sodium bisulfite wash, as determined by GC

| Sodium Bisulfite Solution | Before/After Wash | Acetaldehyde (wtppm) | Acrolein (wtppm) | 3-Buten-2-one (wtppm) | Crotonaldehyde (wtppm) |
|---|---|---|---|---|---|
| 17 wt % $NaHSO_3$ | Before | 58 | 46 | 45 | 55 |
| | After | 0 | 0 | 1 | 0 |
| | Before | 15 | 12 | 12 | 13 |
| | After | 0 | 0 | 0 | 0 |

The results of Table 2 indicate that the 17 wt % sodium bisulfate solution was effective for the removal of acetaldehyde, acrolein, 3-buten-2-one, and crotonaldehyde.

The residual 1 wtppm 3-buten-2-one of Table 2 likely indicated that a carbonyl functional group associated with relatively more steric bulk may slow the sulfite nucleophilic addition. It is believed that extending the mixing time may compensate for this feature.

What is claimed is:

1. A method of treating a mixture, the method comprising:
providing a hydrocarbon mixture comprising one or more C2-C4 carbonyl-containing organic compounds; and
contacting the hydrocarbon mixture with an aqueous liquid comprising an agent, the agent comprising: (i) sodium sulfite ($Na_2SO_3$), (ii) sodium bisulfite ($NaHSO_3$), (iii) sodium metabisulfite ($Na_2S_2O_5$), (iv) sodium borohydride ($NaBH_4$), (v) dimethylacetamide ($CH_3CN(CH_3)_2$), or (vi) a combination thereof;
wherein the one or more C2-C4 carbonyl-containing organic compounds comprise propanal, propenal, butanone, butenone, butanal, butenal, or a combination thereof, and
wherein the hydrocarbon mixture and the aqueous liquid are present at a volume ratio of about 0.5:1 to about 1.5:1.

2. The method of claim 1, further comprising separating the hydrocarbon mixture and the aqueous liquid to form a product hydrocarbon mixture.

3. The method of claim 2, wherein an amount of the one or more C2-C4 carbonyl-containing organic compounds that is present in the product hydrocarbon mixture is about 95% to 100% less than an amount of the one or more C2-C4 carbonyl-containing organic compounds in the hydrocarbon mixture.

4. The method of claim 1, wherein each of the one or more C2-C4 carbonyl-containing organic compounds is independently present in the hydrocarbon mixture at an amount of about 5 wtppm to about 25 wtppm.

5. The method of claim 1, wherein the one or more C2-C4 carbonyl-containing organic compounds comprise acetaldehyde, propenal, 3-buten-2-one, crotonaldehyde, or a combination thereof.

6. The method of claim 5, wherein the acetaldehyde, the propenal, the 3-buten-2-one, and the crotonaldehyde are independently present in the hydrocarbon mixture at an amount of about 5 wtppm to about 25 wtppm.

7. The method of claim 1, wherein the agent is present in the aqueous liquid at an amount of about 10% to about 30% by weight, based on the total weight of the aqueous liquid and the agent.

8. The method of claim 1, wherein the agent is present in the aqueous liquid at an amount of about 15% to about 25% by weight, based on the total weight of the aqueous liquid and the agent.

9. The method of claim 1, wherein the hydrocarbon mixture comprises C4 paraffins, C4 olefins, butadiene, and acetylenes.

10. The method of claim 1, wherein the contacting of the hydrocarbon mixture with the aqueous liquid comprises mixing the hydrocarbon mixture and the aqueous liquid.

11. A method of treating a mixture, the method comprising:
providing a hydrocarbon mixture, the hydrocarbon mixture comprising [1] about 5 wtppm to about 200 wtppm of acrolein, [2] about 5 wtppm to about 200 wtppm of 3-buten-2-one, [3] about 5 wtppm to about 200 wtppm of crotonaldehyde, or [4] a combination thereof;
contacting the hydrocarbon mixture with an aqueous liquid comprising an agent, the agent comprising: (i) sodium sulfite ($Na_2SO_3$), (ii) sodium bisulfite ($NaHSO_3$), (iii) sodium metabisulfite ($Na_2S_2O_5$), (iv) sodium borohydride ($NaBH_4$), (v) dimethylacetamide ($CH_3CN(CH_3)_2$), or (vi) a combination thereof, wherein the hydrocarbon mixture and the aqueous liquid are present at a volume ratio of about 0.5:1 to about 1.5:1; and
separating the hydrocarbon mixture and the aqueous liquid to form a product hydrocarbon mixture;
wherein the product hydrocarbon mixture comprises at least one of acrolein, 3-buten-2-one, or crotonaldehyde at a concentration of 0 wtppm to about 3 wtppm.

12. The method of claim 11, wherein the product hydrocarbon mixture comprises [1] 0 wtppm to about 3 wtppm of acrolein, [2] 0 wtppm to about 3 wtppm of 3-buten-2-one, and [3] 0 wtppm to about 3 wtppm of crotonaldehyde.

13. The method of claim 11, wherein the product hydrocarbon mixture comprises at least one of acrolein, 3-buten-2-one, or crotonaldehyde at a concentration of 0 wtppm to about 1 wtppm.

14. The method of claim 11, wherein the product hydrocarbon mixture comprises [1] less than about 3 wtppm of acrolein, [2] less than about 3 wtppm of 3-buten-2-one, and [3] less than about 3 wtppm of crotonaldehyde.

15. The method of claim 11, wherein the contacting of the hydrocarbon mixture with the aqueous liquid comprises mixing the hydrocarbon mixture and the aqueous liquid.

16. The method of claim 15, wherein the hydrocarbon mixture and the aqueous liquid are present at a volume ratio of about 0.8:1 to about 1.2:1.

17. A method of treating a mixture, the method comprising:
providing a hydrocarbon mixture, the hydrocarbon mixture comprising one or more C2-C4 carbonyl-containing organic compounds, wherein at least one of the one or more C2-C4 carbonyl-containing organic compounds is present at a concentration of about 5 wtppm to about 200 wtppm;
contacting the hydrocarbon mixture with an aqueous liquid comprising an agent, the agent comprising: (i) sodium sulfite ($Na_2SO_3$), (ii) sodium bisulfite ($NaHSO_3$), (iii) sodium metabisulfite ($Na_2S_2O_5$), (iv) sodium borohydride ($NaBH_4$), (v) dimethylacetamide ($CH_3CN(CH_3)_2$), or (vi) a combination thereof, and wherein the hydrocarbon mixture and the aqueous liquid are present at a volume ratio of about 0.5:1 to about 1.5:1;
separating the hydrocarbon mixture and the aqueous liquid to form a product hydrocarbon mixture;
wherein the product hydrocarbon mixture comprises 0 wtppm to about 3 wtppm of the C2-C4 carbonyl-containing organic compound that was present in the hydrocarbon mixture at the concentration of about 5 wtppm to about 200 wtppm.

18. The method of claim 17, wherein the product hydrocarbon mixture comprises 0 wtppm to about 1 wtppm of the C2-C4 carbonyl-containing organic compound that was present in the hydrocarbon mixture at the concentration of about 5 wtppm to about 200 wtppm.

19. The method of claim 17, wherein the agent is present in the aqueous liquid at an amount of about 10% to about 30% by weight, based on the total weight of the aqueous liquid and the agent.

20. The method of claim 17, wherein the contacting of the hydrocarbon mixture with the aqueous liquid comprises mixing the hydrocarbon mixture and the aqueous liquid.

* * * * *